(12) United States Patent
Vanderschot

(10) Patent No.: US 6,299,644 B1
(45) Date of Patent: Oct. 9, 2001

(54) VERTEBRAL REPLACEMENT IMPLANT

(76) Inventor: Paul Vanderschot, Dorpstraat 613 3061 Street, Leefdaal (BE)

( * ) Notice: Subject to any disclaimer, the term of this patent is extended or adjusted under 35 U.S.C. 154(b) by 0 days.

(21) Appl. No.: 09/445,826

(22) PCT Filed: Jun. 16, 1998

(86) PCT No.: PCT/BE98/00094

§ 371 Date: Dec. 14, 1999

§ 102(e) Date: Dec. 14, 1999

(87) PCT Pub. No.: WO98/57601

PCT Pub. Date: Dec. 23, 1998

(30) Foreign Application Priority Data

Jun. 16, 1997 (BE) .................................................. 09700516

(51) Int. Cl.[7] ...................................................... A61F 21/44
(52) U.S. Cl. ........................................................ 623/17.15
(58) Field of Search ............................. 623/17.11, 17.12, 623/17.15; 606/61

(56) References Cited

U.S. PATENT DOCUMENTS

| 4,636,217 | 1/1987 | Ogilvie et al. . |
| 4,874,389 | 10/1989 | Downey . |
| 5,458,641 | * 10/1995 | Ramirez Jimenez ............. 623/17.11 |
| 5,571,192 | * 11/1996 | Schonhoffer ........................ 606/63 X |
| 5,702,455 | 12/1997 | Saggar . |
| 5,989,290 | * 11/1999 | Biedermann et al. ............. 606/61 X |
| 6,015,436 | * 1/2000 | Schonhoffer ........................ 623/17.16 |

FOREIGN PATENT DOCUMENTS

| 4423257 | 1/1996 | (DE) . |
| 19549426 | * 2/1997 | (DE) . |
| 0188954 | 7/1986 | (EP) . |
| 2636227 | 3/1990 | (FR) . |
| 9617564 | 6/1996 | (WO) . |
| 9746165 | 12/1997 | (WO) . |

* cited by examiner

*Primary Examiner*—Bruce Snow
*Assistant Examiner*—Brian E Pellegrino
(74) *Attorney, Agent, or Firm*—Dykema Gossett PLLC

(57) ABSTRACT

A vertebral replacement implant for interposition in a space left by one or more at least partially removed vertebrae between adjacent intact vertebrae. The implant has a connecting body with opposite ends sized to span at least a portion of the space between the intact vertebrae and two end pieces that are provided for attachment to the opposite ends of the connecting body. For anchoring the implant into the adjacent intact vertebrae, a cutting screw blade is provided on the end pieces so that these end pieces can be screwed into the intact vertebrae. In this way, a rigid fixation of the two adjacent intact vertebrae can be obtained thus enabling fusion thereof by bone growth without the use of an additional lateral support assembly.

20 Claims, 3 Drawing Sheets

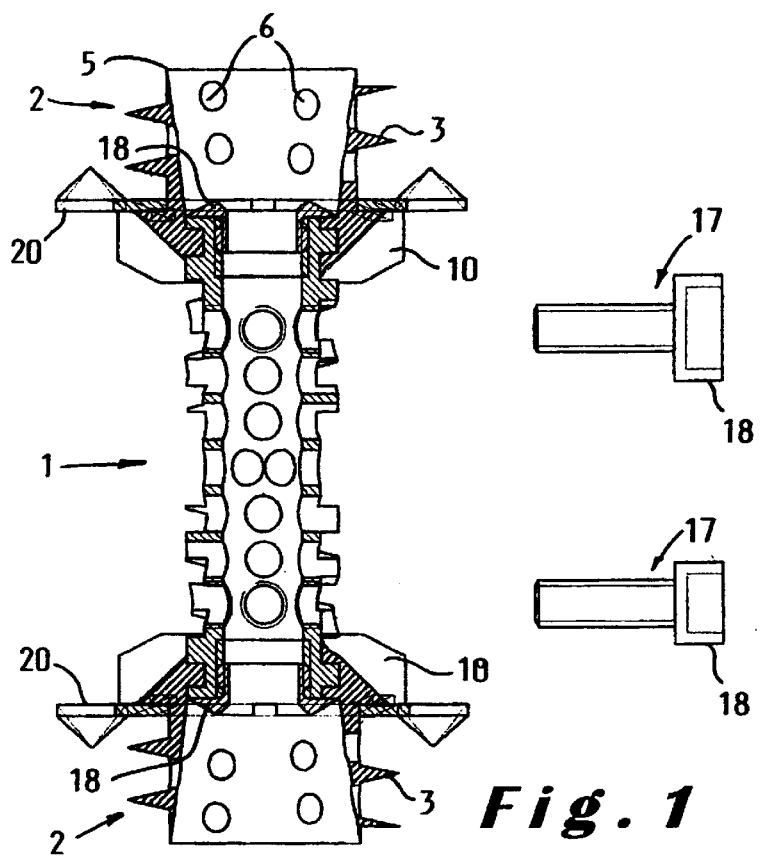
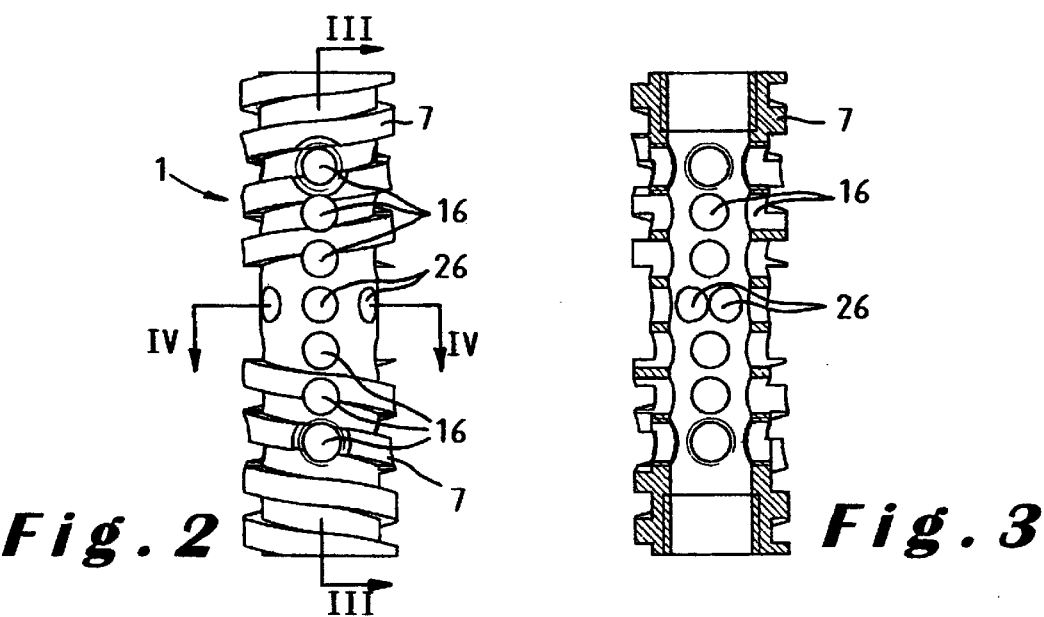
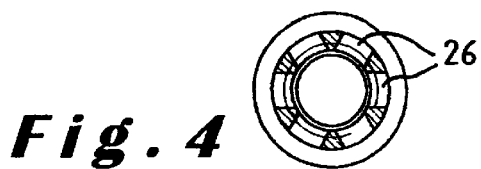

VERTEBRAL REPLACEMENT IMPLANT

The present invention relates to a vertebral replacement implant for interposition in a space left by one or more at least partially removed vertebrae between adjacent intact vertebrae, comprising a connecting body with opposite ends sized to span at least a portion of the space between the intact vertebrae; and two end pieces provided for being fixed to the opposite ends of said connecting body and comprising means for anchoring the implant into the adjacent intact vertebrae.

Such a vertebral replacement implant is already disclosed in WO 96/17564. The known implant comprises a hollow cylindrical connecting body provided at both ends with opposite screw threads onto which two endplates can be screwed. By rotating the connecting body, the two endplates can thus be drawn apart and clamped between the adjacent intact vertebrae. Set screws extending through the endplates into contact with the connecting body are provided for preventing rotation or the connecting body with respect to either of the endplates. The end faces of the endplates include a number of spikes configured to penetrate the end plate of the adjacent vertebral bodies to help maintain the position of the implant in situ.

A drawback of the known implant is that for the fixation of the adjacent intact vertebrae an additional support assembly is still required. This support assembly comprises clamps fixed laterally by means of screws to the intact vertebrae and an elongated distraction or compression rod mounted between these clamps. For applying this additional support assembly, not only the diseased or destroyed vertebra has to be dissected unilaterally but also the two adjacent intact vertebrae. This is a serious operation amongst others because during the dissection, the segmental arteries and veins have to be tied on involving an increased risk for ischemia. A complete fixation of the two adjacent intact vertebrae is however essential for fusing them by new bone growth starting from the bone grafts which are applied in the space between these two vertebrae.

An object of the present invention is now to provide a new type of vertebral replacement implant which enables to fix the two adjacent intact vertebrae sufficiently rigidly to one another that a new bone mass connecting both vertebrae may be developed, in particular without the help of any lateral support arrangements fixed laterally against the intact vertebrae.

To this end, the vertebral replacement implant according to the invention is characterized in that said anchoring means comprise a cutting screw blade provided on the end pieces for screwing these end pieces into the intact vertebrae.

According to the invention it has been found that by making use of a screw blade instead of spikes on the end pieces, the implant can be fixed sufficiently solidly into the adjacent intact vertebrae to prevent any relative movements of both intact vertebrae and hence to connect both vertebrae with new bone growth.

In an advantageous embodiment of the vertebral replacement implant according to the invention, said connecting body has first threads defined thereon at each of said opposite ends and said end pieces second threads configured to threadedly engage the first threads on said connecting body. In this way, a solid connection can easily be obtained between the end pieces and the connecting body.

Moreover, said first and second threads and said cutting screw blade have preferably a substantially equal pitch. According to the invention, it has been found that this feature enables to screw the end pieces much easier into the adjacent vertebrae. Indeed, by rotating the end pieces on the connecting body, they move apart and are thus forced to penetrate in the adjacent vertebrae at the same progression as that determined by the cutting screw blade.

In a further advantageous embodiment of the vertebral replacement implant according to the invention, said end pieces comprise a hollow cylindrical portion onto which said cutting screw blade is provided, the cylindrical portion having an open end for penetrating into a respective one of the intact vertebrae, the open end showing preferably a sharpened edge.

Due to the larger cross-section or diameter which can be achieved by means of the hollow cylindrical portion compared to for example a solid screw, a considerably more stable fixation of the end pieces in the adjacent vertebrae, more particularly against lateral bending stresses, can be realized. Moreover, also the total cross-sectional area of the cutting screw blade is larger thus providing a stronger anchoring of the end pieces, against axial stresses, in the intact vertebrae.

Further particularities and advantages of the invention will become apparent from the following description of some particular embodiments of the vertebral replacement implant according to the present invention. This description is only given by way of illustrative example and is not intended to limit the scope of protection. The reference numerals relate to the annexed drawings wherein:

FIG. 1 shows a longitudinal cross-sectional view of a preferred embodiment of the vertebral replacement implant according to the invention;

FIG. 2 shows a side elevational view of the connecting body of the vertebral replacement implant illustrated in FIG. 1;

FIG. 3 shows a longitudinal cross-sectional view according to lines III—III in FIG. 2;

FIG. 4 shows a lateral cross-sectional view according to lines IV—IV in FIG. 2.

Figure 8:
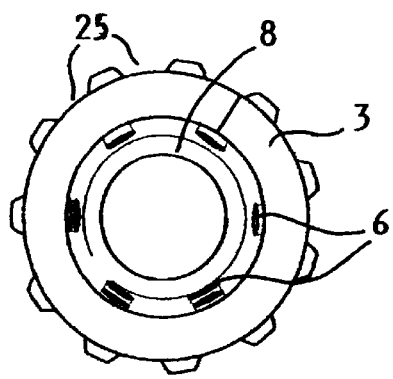
FIG. 8 shows a bottom plan view of the end piece illustrated in FIG. 5.
Figure 5:
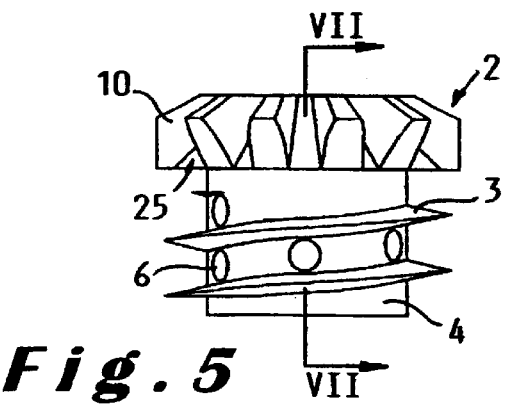
FIG. 5 shows a side elevational view of one of the end pieces of the vertebral replacement implant illustrated in FIG. 1.
Figure 7:
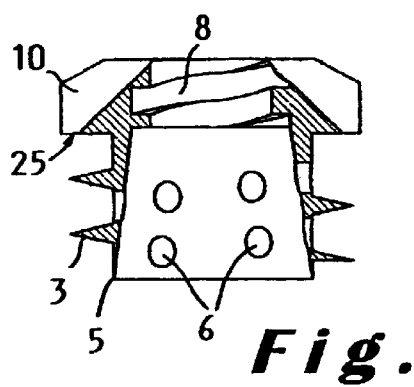
FIG. 7 shows a longitudinal cross-sectional view according to lines VII—VII in FIG. 5.
Figure 6:
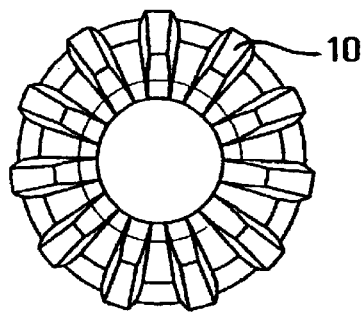
FIG. 6 shows a top plan view of the end piece illustrated in FIG. 5.

The vertebral replacement implant illustrated in the figures is arranged for performing a surgical or endoscopic fusion after corpectomy at the level of the thoracic or lumbar spine. During the corpectomy, a portion of the vertebral body is removed as well as the two adjacent discs. The longitudinal anterior ligament remains normally intact and is maintained.

After the corpectomy, the vertebral replacement implant according to the invention can be positioned through a relatively small surgical incision or even endoscopically into the space left by the partially removed vertebra between the adjacent intact vertebrae. Within and/or along the implant, bone grafts are applied to enable a fusion of the intact vertebrae by bone growth. Such a fusion requires a rigid mutual fixation of the two adjacent vertebrae, which can be achieved by means of the implant illustrated in the figures without an additional fixation by means of lateral support devices arranged on the outside of the spine. This implant can thus be used as a so-called "stand alone device".

The vertebral replacement implant illustrated in the figures comprises more particularly first of all an elongated connecting body 1 and two end pieces 2 mounted onto a respective one of the two ends of the connecting body 1. The end pieces 2 are provided with means for anchoring the implant into the two adjacent intact vertebrae. According to the invention, these anchoring means comprise a cutting screw blade 3 provided on the end pieces 2 for screwing these end pieces into the intact vertebrae. In this way, a rigid fixation between the implant and the adjacent vertebrae can be obtained without the use of an auxiliary lateral supporting device.

The end pieces 2, illustrated more into detail in FIGS. 5 to 8, consist mainly of a hollow, generally cylindrical part 4 onto which the cutting screw blade 3 is provided at the outside. The top of the free extremity of the end pieces is open so that they can penetrate into the adjacent vertebrae. In order to assist penetration of the end pieces in the vertebrae, their open top end is preferably formed by a sharpened edge 5. It has been found that such an end piece 2 can be screwed into intact vertebrae without crushing the bone material, either within or outside the end piece. The cylindrical wall of the end piece is further preferably perforated with apertures 6 to provide flow of blood to and from the enclosed bone tissue. In this way this bone tissue can be kept intact and may contribute in the fixation of the implant and in the fusion by bone growth between the two intact vertebrae.

In the embodiment shown in the figures, the end pieces 2 are rigidly fixed onto the connecting body 1 by means of co-operating screw threads provided on the end pieces 2 and on the connecting body 1. The connecting body 1 has more particularly first threads 7 defined on the outside thereof at each of its opposite ends and the end pieces 2 second threads 8 defined on the inner wall of the hollow part 4 thereof. In an alternative, less preferred embodiment, the end pieces 2 may be slidably connected to the connecting body 1 and for example set screw may be provided for fixing these components together once the end pieces have been screwed in the intact vertebrae.

According to the invention, the first and second threads have advantageously a pitch which is equal to the pitch of the screw blade 3. In this way, when screwing the end pieces in the intact vertebrae, they are forced to penetrate therein at the speed or progression defined by the pitch (and the rotational speed) of the cutting screw blade 3. It has been found that, by applying the required rotational forces onto the end pieces 2 while maintaining the connecting body in position, the end pieces can easily be screwed in the intact vertebrae with a minimal damage to these vertebrae. Preferably, the first threads 7 at the opposite ends of the connecting body 1 have an opposite screwing direction so that, before screwing the end pieces 2 into the intact vertebrae, they can be clamped therebetween by rotating the connecting body 1 itself. However, when subsequently screwing the end pieces 2 into the intact vertebrae, the connecting body 1 is not rotated but only the end pieces 2.

Figure 12:
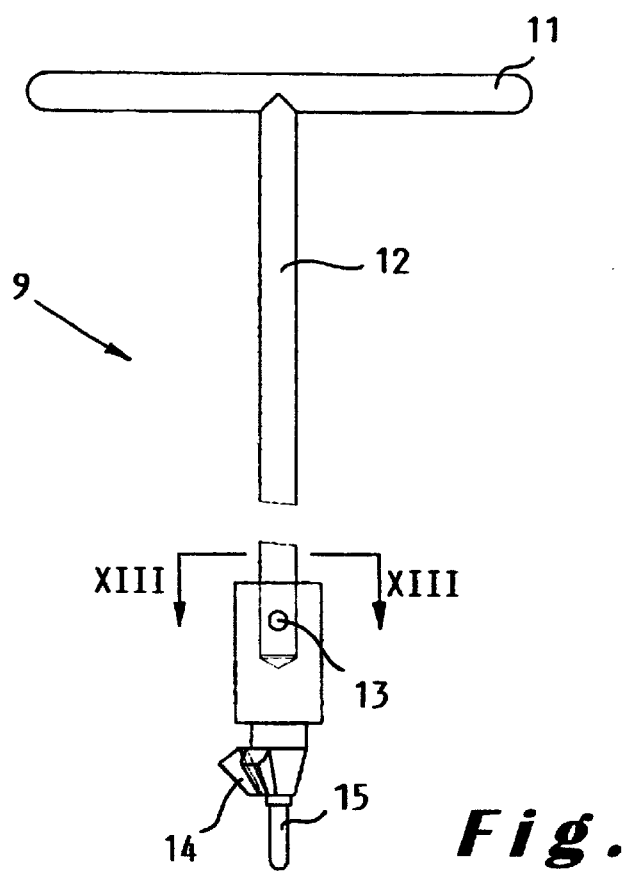
FIG. 12 shows a side elevational view of a chuck key used for rotating the end pieces of the vertebral replacement implant illustrated in FIG. 1 around the connecting body thereof.
Figure 13:
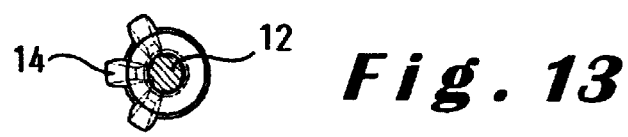
FIG. 13 shows a cross-sectional view according to lines XIII—XIII in FIG. 12.

In the embodiment shown in the figures, the end pieces 2 can be screwed endoscopically into the intact vertebrae by means of a chuck key 9 co-operating with a crown wheel 10 provided on the end pieces 2. This crown wheel 10 is situated in a plane perpendicular to a longitudinal symmetry axis of the end pieces. A possible chuck key 9 has been illustrated in FIGS. 12 and 13 and comprises a handle 11, an elongated shaft 12 fixed at its distal extremity through the intermediary of a shaft key 13 to the actual key tool. This tool comprises a preferably partial crown wheel 14 with only three teeth. At its distal extremity, the key is extended with a cylindrical projection 15.

For keeping the teeth of the crown wheel 14 on the chuck key 9 engaged in the teeth of the crown wheel 10 when screwing the respective end piece 2 in the intact vertebra, four rows of holes 16 are provided in the connecting body 1 and are arranged to receive the terminal projection 15 on the chuck key 9. When screwing the end piece 2 in, the chuck key 9 will successively be inserted into the different holes 16. If necessary, two or more chuck keys 9 can be provided, having crown wheels 14 with a different height of teeth, in order to bridge the gap between the different holes 16.

The most terminal hole 16 of the different row of holes is an internally threaded boring wherein a bolt 17 can be screwed for locking the end piece 2 in its extreme position. The bolt 17 has more particularly a head 18 which may penetrate between the teeth of the crown wheel 10 on the end piece so that any rotation of the end piece 2 on the connecting body 1 is prevented.

Figure 9:
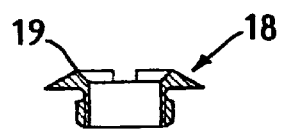
FIG. 9 shows a longitudinal cross-sectional view of one of the steps of the vertebral replacement implant illustrated in FIG. 1.

In order to avoid the risk of unscrewing the end pieces 2 entirely from the connecting body 1, the illustrated replacement implant comprises two stops 18 arranged to be screwed into the respective ends of the connecting body 1. Alternatively, the stops 18 could also be screwed on an externally threaded end portion of the connecting body but this embodiment has not been shown. The stops 18 of the illustrated embodiment, shown more into details in FIG. 9, are generally formed by a hollow bolt. When being screwed in the connecting body, the head or top surface 19 of this bolt project laterally from the core of the connecting body so as to form an abutment for the respective end piece. The direction of the screw thread on the stop 18 is opposite to the screw direction of the second thread in the end piece 2 so that, when this end piece 2 is unscrewed until it engages the stop 18, it does not unscrew the stop 18 but instead tightens it further. The top surface 19 of the stops 18 are preferably conical or dome-shaped which facilitates applying the implant and centering it in the space between the two intact vertebrae.

Figure 10:
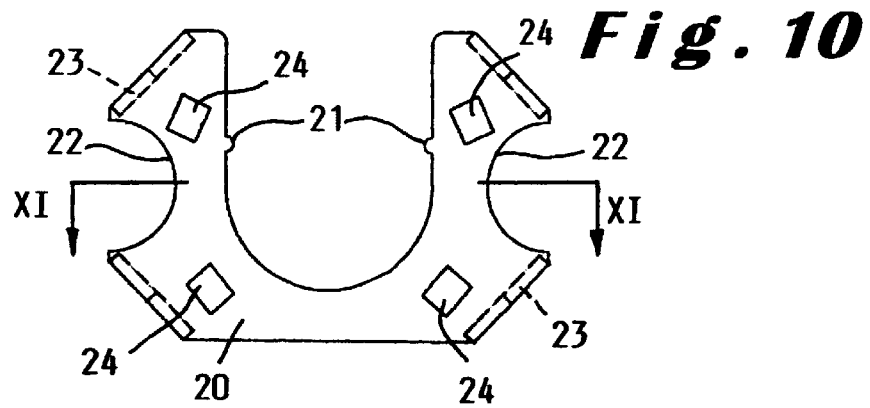
FIG. 10 shows a bottom view of one of the retainer plates of the vertebral replacement implant illustrated in FIG. 1.
Figure 11:
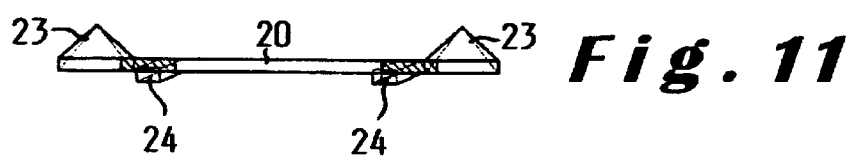
FIG. 11 shows a cross-sectional view according to line XI—XI in FIG. 10.

A further component of the implant illustrated in the figures is a retainer plate 20 shown more into detail in FIGS. 10 and 11. This retainer plate 20 is applied on the end pieces 2, between the screw blade 3 and the crown wheel 10. It preferably forms an open ring which can be snapped laterally over the end piece and comprises for example lugs 21 for locking it on the end piece 2.

A first aim of the retainer plate 20 is to increase the bearing surface of the implant. In the shown embodiment, the surface area of the retainer plate is however locally reduced by recesses 22 in the edge thereof. Those recesses are intended to leave the necessary space for applying bone grafts and thus for allowing fusion of the intact vertebrae. An advantage of the implant according to the present invention is indeed that the connecting body 1 may have a limited diameter leaving thus sufficient space for applying bone grafts along the connecting body.

A further aim of the retainer plate shown in the figures consists in preventing a rotational motion of the end piece with respect to the intact vertebra wherein it is screwed. This retainer plate 20 has more particularly projections 23 on the four corners directed to the screw blade 3 and thus arranged for penetrating in the intact vertebra when the end piece 2 is screwed therein. On the other side, the retainer plate 20 is provided with locking means consisting in particular of locking cams 24 which slide over notches 25, in particular over the teeth of the crown wheel 10, when screwing the end piece 2 into the vertebra, but which do not allow unscrewing thereof. The projections 23 are formed by folding the corners of the retainer plate 20 whilst the locking cams 24 are formed by partially punching rectangular parts out off the retainer plate and folding these parts somewhat downwards as can be seen in FIG. 11. Due to the irrotatable connection between the retainer plate 20 and the intact vertebra, and between the retainer plate 20 and the end piece 2 (once the end piece 2 has been screwed entirely in the intact vertebra), the end pieces 2 are irrotatably fixed into the intact vertebra. By means of the bolts 17, the end pieces 2 are further irrotatably fixed onto the connecting body 1 so that the implant as a whole prevents any mutual rotation of the two adjacent intact vertebrae.

As explained hereabove, compression of the spine is prevented by the bearing power of the cutting screw blades 3 in the intact vertebrae and, additionally, by the bearing power of the retainer plates 20. On the other hand, distraction of the spine at the level of the implant is avoided again by the fixation of the cutting screw blades 3 in the intact vertebrae. Moreover, before inserting the implant, the vertebrae are somewhat distracted so that the anterior ligament, which remains intact, is tensioned and also helps preventing further distraction of the spine.

For applying the implant according to the invention in the space between two intact vertebrae, these two vertebrae are advantageously first somewhat distracted by means of for example a distraction forceps. This requires some fixation to the intact vertebrae but not a real support assembly which is as large as in WO96/17564. In fact, the intact vertebrae have to be dissected only very locally.

The implant which will be applied in the space between the two intact vertebrae comprises preferably a connecting body 1, the height of which is substantially equal to the distance between the two intact vertebrae. Before applying the implant, the end pieces 2 are screwed as far as possible thereon, in particular so far that the conical or dome-shaped top surface 19 of the stops 18, which are subsequently screwed in the connecting body 1, form the end faces of the implant. In this way, the implant, having further the retainer plates 20 snapped thereon, can easily be positioned in the space between the two intact vertebrae. This can either be done surgically, through a relatively small insertion, or even endoscopically. For facilitating handling the implant, the connecting body 1 is, in the middle, preferably provided with a ring of openings 26, for example six openings, wherein the jaws of a suitable forceps may penetrate to firmly hold the implant. By means of this forceps, the connecting body 1 may be rotated somewhat in order to clamp the implant between the two intact vertebrae.

Subsequently, the forceps are removed and the chuck key 9 is introduced endoscopically in the body. This may be done in particular transthoracically or retroperitoneally. Rotation of the crown wheel 14 or, in other words, of the chuck key 9 to screw the end pieces as explained hereabove in the intact vertebrae, can be performed easily from outside the body. The crown wheel 14 may be a partial crown wheel in order to engage the crown wheel 10 of one end piece 2 only when the end pieces are screwed entirely onto the connecting body 1. On the other hand, one may also consider using a chuck key 9 with a complete crown wheel 14 by which, in an initial phase, the two end pieces can be screwed simultaneously in the adjacent vertebrae in view of their opposite screw direction.

When use is made of a connecting body 1 having a height substantially equal to the distance between the two intact vertebrae, the end pieces 2 can be screwed over a maximum depth therein thus providing a maximum fixation force.

From the above description, it will be clear that the invention is not limited to the described and illustrated embodiment, but that many modifications can be applied thereto provided they fall within the scope of the appended claims.

For example, although preference is given to a hollow, tubular connecting body so that bone grafts can also be applied therein, use could also be made of a solid connecting body, i.e. of a threaded solid rod, having in particular an even smaller diameter than the illustrated hollow body so that more space is available outside the implant for bone fusion.

What is claimed is:

1. A vertebral replacement implant for interposition in a space left by one or more at least partially removed vertebrae between adjacent intact vertebrae, comprising a connecting body with opposite ends sized to span at least a portion of the space between the intact vertebrae, and two end pieces provided for being fixed to the opposite ends of said connecting body and comprising means for anchoring the implant into the adjacent intact vertebrae, wherein said end pieces show a hollow cylindrical portion and said anchoring means comprise a cutting screw blade projecting laterally provided on the hollow cylindrical portions of the end pieces for screwing these end pieces by rotating them into the intact vertebrae, which cylindrical portion has an open end for penetrating into a respective one of the intact vertebrae.

2. The vertebral replacement implant as claimed in claim 1, wherein said open ends of the cylindrical portions of the end pieces show a sharpened edge.

3. The vertebral replacement implant as claimed in claim 1, wherein said connecting body has first threads defined thereon at each of said opposite ends and said end pieces second threads configured to threadedly engage the first threads on said connecting body.

4. The vertebral replacement implant as claimed in claim 3, wherein said first and second threads and said cutting screw blade have a substantially equal pitch.

5. The vertebral replacement implant as claimed in claim 3, wherein the first threads at the opposite ends of the connecting body have an opposite direction.

6. The vertebral replacement implant as claimed in claim 3, further comprising means for locking said connecting body to each of said end pieces to prevent unthreading of said first and second threads.

7. The vertebral replacement implant as claimed in claim 6, wherein said locking means comprise threaded borings in the connecting body and bolts arranged to be screwed therein in engagement with the respective end piece.

8. The vertebral replacement implant as claimed in claim 3, comprising two stops arranged to be screwed to a respective one of the opposite ends of the connecting body and to project laterally so as to form an abutment for the respective end piece to prevent screwing the end piece off the connecting body.

9. The vertebral replacement implant as claimed in claim 8, wherein said stops have a substantially conical or dome-shaped top surface arranged for covering the respective end face of the connecting body.

10. The vertebral replacement implant as claimed in claim 1, wherein said end pieces comprise a crown wheel situated in a plane perpendicular to a symmetry axis of the second threads and the connecting body comprises borings arranged for receiving a chuck key arranged for co-operating with said crown wheel to screw the respective end piece into the adjacent vertebra.

11. The vertebral replacement implant as claimed in claim 1, comprising at least one retainer plate arranged for being applied onto a respective one of said end pieces, behind said screw blade.

12. The vertebral replacement implant as claimed in claim 11, wherein the retainer plate forms an open ring configured such that it can be snapped laterally, behind the screw blade, over the end piece.

13. The vertebral replacement implant as claimed in claim 11, wherein said retainer plate has projections directed towards the screw blade and penetrating into the adjacent vertebra when screwing the end piece therein.

14. The vertebral replacement implant as claimed in claim 13, wherein said retainer plate is provided with locking means co-operating with the end piece for preventing unscrewing thereof.

15. The vertebral replacement implant as claimed in claim 14, wherein said locking means comprise locking cams co-operating with notches in the end piece or vice versa.

16. The vertebral replacement implant as claimed in claim 11, wherein said retainer plate has an edge showing at least one recess for applying a bone graft therein.

17. The vertebral replacement implant as claimed in claim 1, wherein said connecting body comprises a hollow rod.

18. The vertebral replacement implant as claimed in claim 17, wherein said hollow rod has a wall provided with holes for enabling growth of bone within the hollow rod.

19. The vertebral replacement implant as claimed in claim 1, wherein said connecting body has a height substantially equal to the distance between the adjacent intact vertebrae.

20. A vertebral replacement implant for interposition in a space left by one or more at least partially removed vertebrae between adjacent intact vertebrae in a spine, the implant comprising:

a connecting body with opposite ends sized to span at least a portion of the space between the intact vertebrae;

two end pieces provided for being fixed to the opposite ends of said connecting body, said end pieces show a hollow cylindrical portion; and anchoring means for anchoring the implant into the adjacent intact vertebrae, said anchoring means comprising
a cutting screw blade projecting laterally provided on the hollow cylindrical portions of the end pieces, said cutting screw blade preventing compression and a distraction on the spine, and
said cutting screw blade for screwing said end pieces into the intact vertebrae, wherein said cylindrical portion has an open end for penetrating into a respective one of the intact vertebrae.

* * * * *